United States Patent
Top et al.

(10) Patent No.: US 10,478,087 B2
(45) Date of Patent: Nov. 19, 2019

(54) OPEN BORE FIELD FREE LINE MAGNETIC PARTICLE IMAGING SYSTEM

(71) Applicant: ASELSAN ELEKTRONIK SANAYI VE TICARET A.S., Yenimahalle, Ankara (TR)

(72) Inventors: Can Baris Top, Ankara (TR); Huseyin Emre Guven, Ankara (TR)

(73) Assignee: ASELSAN ELEKTRONIK SANAYI VE TICARET A.S., Yenimahalle, Ankara (TR)

( * ) Notice: Subject to any disclaimer, the term of this patent is extended or adjusted under 35 U.S.C. 154(b) by 214 days.

(21) Appl. No.: 15/435,208

(22) Filed: Feb. 16, 2017

(65) Prior Publication Data
US 2018/0231629 A1    Aug. 16, 2018

(51) Int. Cl.
  *A61B 5/05*    (2006.01)
(52) U.S. Cl.
  CPC .................. *A61B 5/0515* (2013.01)
(58) Field of Classification Search
  CPC .................................. A61B 5/0515
  See application file for complete search history.

(56) References Cited

U.S. PATENT DOCUMENTS

| | | | | |
|---|---|---|---|---|
| 4,829,252 A * | 5/1989 | Kaufman | ............... | G01R 33/28 324/309 |
| 5,280,248 A * | 1/1994 | Zou | .................. | G01R 33/34061 324/318 |
| 6,215,307 B1 * | 4/2001 | Sementchenko | ...... | G01R 33/34 324/318 |
| 6,249,121 B1 * | 6/2001 | Boskamp | ......... | G01R 33/34061 324/318 |
| 6,420,871 B1 * | 7/2002 | Wong | ............... | G01R 33/34046 324/318 |
| 6,437,567 B1 * | 8/2002 | Schenck | .......... | G01R 33/34061 324/318 |

(Continued)

FOREIGN PATENT DOCUMENTS

| | | |
|---|---|---|
| WO | 2008078257 A2 | 7/2008 |
| WO | 2013088413 A1 | 6/2013 |

OTHER PUBLICATIONS

Gleich, Bernhard, et al., "Tomographic imaging using the nonlinear response of magnetic particles", 2005 Nature Publishing Group, vol. 435|Jun. 30, 2005|doi:10.1038/nature03808, pp. 1214-1217.

(Continued)

*Primary Examiner* — Dixomara Vargas
(74) *Attorney, Agent, or Firm* — Notaro, Michalos & Zaccaria P.C.

(57) ABSTRACT

An open bore coil system enabling electronic steering and rotation of a Field Free Line (FFL) inside a large volume. An FFL is generated by placing two parallel coil pairs (fed with alternating current directions) side by side. Using two of these coil groups, the FFL can be rotated in the plane perpendicular to the coil axes. The FFL can be translated in the rotation plane of the FFL using a coil pair placed on the same axis with the other coils. It can also be translated in the perpendicular plane by asymmetrical coil excitation. As all the coils in the system are parallel, the imaged object can be reached from the sides during imaging.

25 Claims, 6 Drawing Sheets

(56) References Cited

U.S. PATENT DOCUMENTS

| | | | | |
|---|---|---|---|---|
| 6,580,274 | B2* | 6/2003 | Sato | G01R 33/3657 324/307 |
| 6,650,117 | B2* | 11/2003 | Hoshino | G01R 33/341 324/318 |
| 6,750,654 | B2* | 6/2004 | Sato | G01R 33/34046 324/318 |
| 6,781,371 | B2* | 8/2004 | Taherian | G01N 24/081 324/303 |
| 6,954,069 | B2* | 10/2005 | Harvey | G01R 33/3415 324/318 |
| 7,365,542 | B1* | 4/2008 | Rohling | G01R 33/34084 324/318 |
| 9,008,749 | B2* | 4/2015 | Buzug | A61B 5/0515 600/409 |
| 9,044,160 | B2 | 6/2015 | Knopp et al. | |
| 9,664,757 | B2* | 5/2017 | Sugiyama | G01R 33/385 |
| 2014/0159712 | A1 | 6/2014 | Graziani et al. | |
| 2014/0266172 | A1 | 9/2014 | Hong et al. | |
| 2014/0306998 | A1 | 10/2014 | Bontus et al. | |

OTHER PUBLICATIONS

Knopp, T., et al., "A Fourier slice theorem for magnetic particle imaging using a field-free line", 2011 IOP Publishing Ltd, Inverse Problems 27 (2011) 095004 (14pp).

Konkle, Justin J., et al., Projection Reconstruction Magnetic Particle Imaging, 2012 IEEE, IEEE Transactions on Medical Imaging, vol. 32, No. 2, Feb. 2013, pp. 338-347.

Murase, Kenya e al., Development of a system for magnetic particle imaging using neodymium magnets and gradiometer, 2014 The Japan Society of Applied Physics, Japanese Journal of Applied Physics 53, 067001 (2014).

Rahmer, Jurgen, et al., "Signal encoding in magnetic particle imaging: properties of the system function", 2009 Rahmen et al; licensee BioMed Central Ltd., BMC Medical Imaging 2009, 9:4 doi:10.1186/1471-2342-9-4.

Saritas, Emine U., et al., "Magnetostimulation Limits in Magnetic Particle Imaging", 2013 IEEE, IEEE Transactions on Medical Imaging, vol. 32, No. 9, Sep. 2013, pp. 1600-1610.

\* cited by examiner

OPEN BORE FIELD FREE LINE MAGNETIC PARTICLE IMAGING SYSTEM

FIELD AND BACKGROUND OF THE INVENTION

The present invention relates generally to the field of Magnetic Particle Imaging, and in particular to an open bore coil system enabling electronic steering and rotation of a Field Free Line (FFL) inside a large volume.

Magnetic Particle Imaging (MPI) is an imaging method, which images the concentration of Super Paramagnetic Iron Oxide (SPIO) particles inside a volume of interest. The SPIO nanoparticles can be injected intravenously, or administered orally to the patient/object. It has several potential uses for medical imaging such as angiography, stem cell tracking, and tumor detection.

In the MPI method, the object is placed inside a magnetic field, which includes a field free region (FFR). In this region, the magnetic field strength is very low so that if there are SPIO nanoparticles in this region, their magnetization is not saturated. (i.e. their magnetization can be increased or decreased parallel to the applied magnetic field). This field with the FFR is called the Selection Field (SF), since it is used to select the region in space where the SPIO particles are responsive. The magnetic field with the FFR can be generated using two parallel coils fed with alternating current directions, or using two permanent magnets placed parallel with the same poles looking at each other. The FFR generated with this configuration has an elliptical shape. The magnetization curve of the SPIO particles is non-linear and can be modeled by the Langevin function. This method was first described in Gleich and Weizenecker, "Tomographic imaging using the nonlinear response of magnetic particles," *Nature, vol.* 435, 2005.

Because of the super paramagnetic properties of the nanoparticles, their magnetization can be saturated at moderate magnetic field intensity levels. The particles outside the FFR region are saturated because of the higher magnetic field intensity outside the FFR. (i.e. outside the FFR magnetic field strength is high so that the magnetization of the SPIO nanoparticles cannot increase further with increasing magnetic field strength). If a dynamic magnetic field (which is called the Drive Field-DF) is imposed on the SF, the particles inside the FFR respond by aligning their magnetization with the applied field. On the contrary, the particles in the saturated region are not responsive as their magnetization is not affected by the DF. Change in magnetization vector inside the FFR induces a voltage on the receive coil(s). The induced voltage depends linearly on the particle concentration inside the FFR, which can be reconstructed. The coupled signal from the transmit coil(s) to the receive coil(s) is much larger than the received SPIO response. However, as the magnetization response of the particles is non-linear, the received signal includes the harmonics of the excitation frequency. Generally, the fundamental frequency component is filtered out, and the harmonic frequency components are used to reconstruct the particle concentration.

The FFR can be scanned in 3D to obtain 3D SPIO concentration images. This can be done using drive fields in three orthogonal axes. The homogeneous DF can be generated with two parallel coils fed with the same current (Helmholtz coil configuration). Alternatively, a solenoid structure can also be used. The Helmholtz coils can be placed conformally on a tube with circular cross section.

The amplitude and frequency of the DF should be selected to be in safe limits. There are two effects of the applied DF on the biological tissues: peripheral nerve stimulation (PNS) and heating. It was reported that the PNS can be observed at about 15 mT magnetic field intensity in the frequency region commonly used for MPI (25-50 kHz). (E. U. Saritas et al., "Magnetostimulation Limits in Magnetic Particle Imaging," IEEE Trans. Med. Imag., Vol. 32, no. 9, September 2013). The heating effect depends on the duration and frequency of the dynamic excitation, increasing with both variables. The field of view (FOV) using safe DF amplitude levels is on the order of millimeters. It is possible to steer the FFR inside the object in discrete positions, or continuously with a very low frequency inside safety limits using a homogenous field. This relatively high amplitude and low frequency field is called the Focus Field (FF). A high frequency, lower amplitude DF is applied on top of this field to get the signal from the steered FFR. Extra coils can be used to create the FF. Alternatively, SF or DF coils can be used to generate the FF.

To use MPI method in clinical applications such as angiography, the doctor/medical personnel should be able to physically access the patient to control and direct the process. The vast majority of the MPI systems presented up to date use closed bore scanners, in which the object is placed inside a cylindrical bore and, therefore, not accessible.

The FFR in the MPI method, also called the Field Free Point (FFP), is in the shape of an ellipse with dimensions on the order of millimeters. Since the received signal is induced by the nanoparticles inside this region, the signal level increases with increasing FFR size. However, this contradicts with the image resolution, which decreases with FFR size. The FFP should be scanned in three dimensions, which is a time consuming task especially for relatively large objects such as human body. In a clinical environment, imaging duration should be kept as small as possible to enable real time imaging and to prevent image distortions caused by patient movement.

In summary, even though the MPI field is rapidly developing, the prototypes or products up to date are limited to closed bore scanners with a small FOV size only suitable for small animal experiments. To use the MPI method in the clinic, a fast open bore scanner with a large FOV size is required. In addition, the applied magnetic field levels should be kept below safety limits.

Thus, there is a need for a coil system, which can provide Selection, Focus and Drive fields to meet these clinical requirements.

Prior Art Efforts to Address the Above-Identified Problems

There are a few open bore or single sided MPI systems present in the current state of art.

In U.S. Pat. No. 9,008,749, a single sided MPI system is proposed. The FFP is generated using two different sized electromagnetic coils (one placed inside the other) fed with currents in opposite directions. The DF and FF are also generated with the coils placed on the same side, enabling 3D electronic FFP steering. Usage of a transmitter coil array is proposed to increase the FOV size.

In U.S. Patent Publication 2014/0266172, an open bore MPI system is proposed. In this system, the magnetic field is applied in two different frequencies and the reception is done at an intermodulation product of these frequencies. The image is generated by moving the object mechanically. Although this method has advantages such as low magnetic field level and high sensitivity, it is not suitable for clinical usage as the object should be small and also scanned mechanically.

In U.S. Patent Publication 2014/0306698, an MPI coil system with a large FOV suitable for human imaging is proposed. In this system, there is a center primary coil group, and a secondary coil group placed in a circular configuration outside the primary group. The center coil group generates the SF and scans the FFP in the vertical direction. The secondary group is used to scan the FFP in the horizontal direction. Three different DF are generated for 3 axes scanning. It is mentioned that the DF coils can be made flexible and placed on the patient enabling access to the patient from the sides.

All methods above use FFP as the FFR. In U.S. Pat. No. 9,044,160, usage of Field Free Line (FFL) is proposed. Field Free Line defines a tubular volume with ellipsoidal, cylindrical, or arbitrarily-shaped cross section where the magnetic field is very low such that the SPIO nanoparticles' magnetization is not saturated. In practice, the central path of this tubular volume can be linear, partially linear, or non-linear. The main advantages of FFL over FFP are higher sensitivity and shorter imaging time. To generate images with the FFL, it should be rotated to cover at least 180 degrees with step size depending on the required image resolution, and also translated at each angle in the whole imaging plane (or volume). In the method given in U.S. Pat. No. 9,044,160, the FFL is generated using 8 coils placed circularly around the object. It can be rotated by adjusting the currents of the coils, and translated using extra DF coils. The FFL can also be generated using permanent magnets (Konkle et al., "Projection Reconstruction Magnetic Particle Imaging," IEEE Trans. Med. Imag, vol. 32, no. 2, February 2013., Murase K, Hiratsuka S, Song R, Takeuchi Y. Development of a system for magnetic particle imaging using neodymium magnets and gradiometer. Jpn J Appl Phys. 2014; 53(6):067001). However, the FFL cannot be rotated electronically and mechanical rotation of the object is necessary for 3D imaging.

The single sided MPI systems in the prior art enable patient access and electronical FFR scanning. However, these methods use a point FFR (i.e. FFP). Therefore, for a large volume coverage sensitivity and imaging duration are possible issues for these systems. MPI methods employing FFL attempt to provide a solution to these problems. Nevertheless, the proposed FFL systems rather require coils around the object preventing access, or require mechanical rotation which is not feasible clinically.

SUMMARY OF THE INVENTION

Thus, it is an object of the present invention to provide an open bore coil system which enables access to the patient/object for intervention during imaging using a fully electronically scanned FFL for high sensitivity and rapid imaging, enabling MPI method to be used for 3D imaging in a clinical environment It is also an object of the present invention to provide a system which achieves imaging a large FOV inside acceptable safety limits.

It is a further object of the invention to provide access to the patient/object during the MPI procedure.

Further still, it is an object to image a large volume in a small time in an open bore configuration.

Accordingly, in the present invention an FFL is generated by placing two parallel coil pairs (fed with alternating current directions) side by side. Using two of these coil groups, the FFL can be rotated in the plane perpendicular to the coil axes. The FFL can be translated in the rotation plane of the FFL using a coil pair placed on the same axis with the other coils. It can also be translated in the perpendicular plane by asymmetrical coil excitation. As all the coils in the system are parallel, the imaged object can be reached from the sides during imaging.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

The following is a brief description of the drawings, which are presented for the purposes of illustrating the exemplary embodiments disclosed herein and not for the purposes of limiting the same.

DESCRIPTION OF THE PREFERRED EMBODIMENTS

Figure 1:
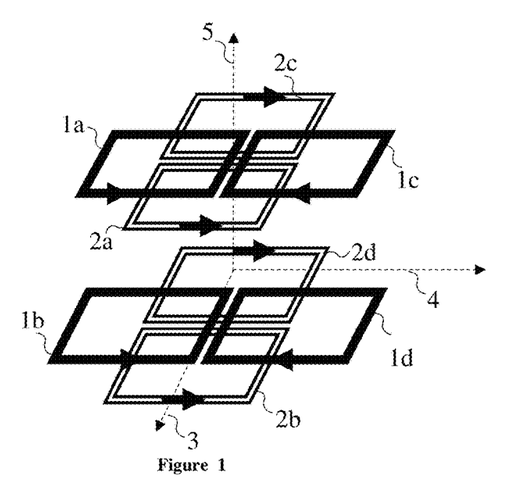
FIG. 1 shows a coil system and respective current directions enabling to generate, rotate and translate a field free line for MPI.
Figure 2:
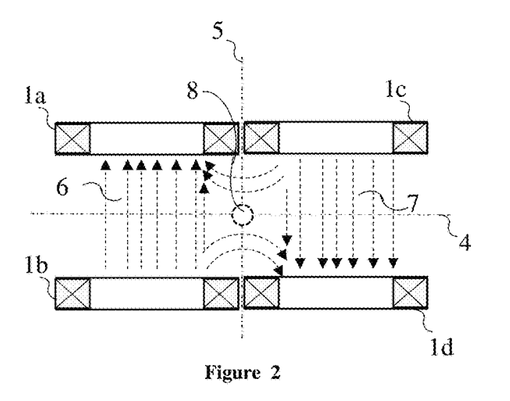
FIG. 2 shows the x=0 plane cut for the coil group (1) in FIG. 1 and respective magnetic field lines used for generating an FFL in the x-axis direction.
Figure 3A:
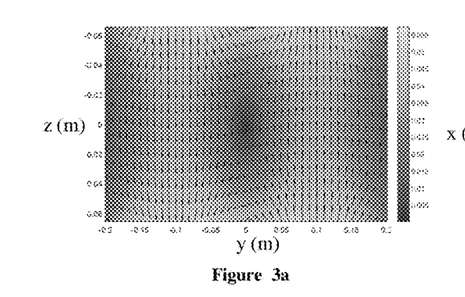
FIG. 3a shows the simulation result of the magnetic field intensity and vector for the coils group shown in FIG. 2 at x=0 plane cut.
Figure 3B:
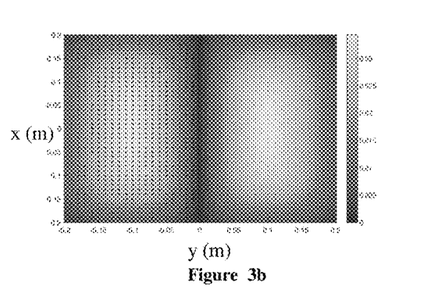
FIG. 3b shows the simulation result of the magnetic field intensity and vector for the coils group shown in FIG. 2 at z=0 plane cut.

The selection field coils for the proposed coil system for open bore FFL arrangement consists of 2 coil groups (1, 2). Coils (1a), (1b), (1c), and (1d) form coil group (1) and are fed with currents I1a, I1b, I1c, and I1d, respectively (FIG. 1). Coils (2a), (2b), (2c), and (2d) form coil group (2) and are fed with currents I1a, I2b, I2c, and I2d, respectively. The coils in a coil group are located as coil pairs placed side by side and fed with alternating current directions (FIG. 1). The magnetic field distribution for the coil group (1) is shown in FIG. 2 on the plane generated by the y (4) and z (5) axes (Coil group 2 is not excited in this case). Coils (1a) and (1b) are fed with the same current direction generating a magnetic field in the z-direction (6). Coils (1c) and (1d) are fed with opposite current direction with respect to the (1a-1b) coil pair, generating a magnetic field in the −z direction (7). The x (3) and y (4) components of the magnetic field vanish at the middle plane (the plane generated by the x (3) and y (4) axes) of the top (1a4c) and bottom (1b, 1d) coils. The z-axis component of the magnetic field vanishes at the mid-plane (the plane generated by the x (3) and z (5) axes) between coil pairs (1a-1b) and (1c-1d). Therefore, an FFL (8) is generated, which is aligned along the x-axis (3). The magnetic field distribution obtained using a computer simulation model for such a configuration is shown in FIG. 3. FIG. 3a shows the magnetic field distribution on the plane generated by the y (4) and z (5) axes. FIG. 3b shows the magnetic field distribution on the plane generated by the x (3) and y (4) axes.

Figure 4:
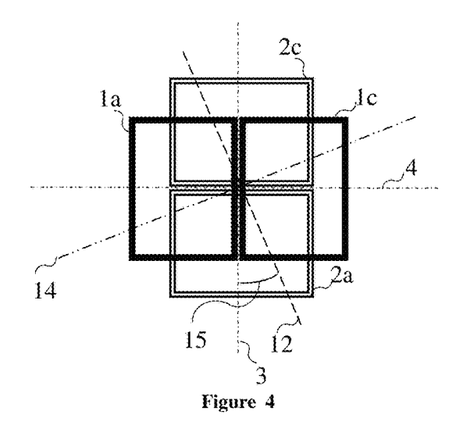
FIG. 4 shows the coil system in FIG. 1 looking from z-axis (5)

Coil group 2 (2) has a similar configuration with the coil group (1), but is rotated 90 degrees around z-axis (5). In FIG. 4, the coil system given in FIG. 1 is shown looking into the z-axis (5). The FFL can be rotated to any arbitrary angle θ (15) with respect to x-axis (3) on the plane generated by the x (3) and y (4) axes by adjusting the currents of the coil groups (1) and (2). In FIG. 4, (12) shows the direction of the FFL, and (14) shows the direction perpendicular to the FFL direction. If the coil group (2) is not excited, the FFL is generated on the x axis (3) and θ=0 degrees. Similarly, if the coil group 1 (1) is not excited, the FFL is generated on the y axis (4) and θ=90 degrees. In general, to rotate the FFL θ degrees (15) with respect to x-axis (3), the excitation for the coils in the coil group (1) should be: I1a=I1b=−I1c=−I1d=I$_1$ cos(phi). Similarly, the excitation of the coils in the coil group (2) should be I2a=I2b=−I2c=−I$_2$d=I$_2$ sin(phi). In the preferred embodiment, the current amplitudes I$_1$ and I$_2$ should be arranged such that the magnetic field gradient perpendicular to the FFL axis (14) is independent of the rotation angle (15).

Figure 5:
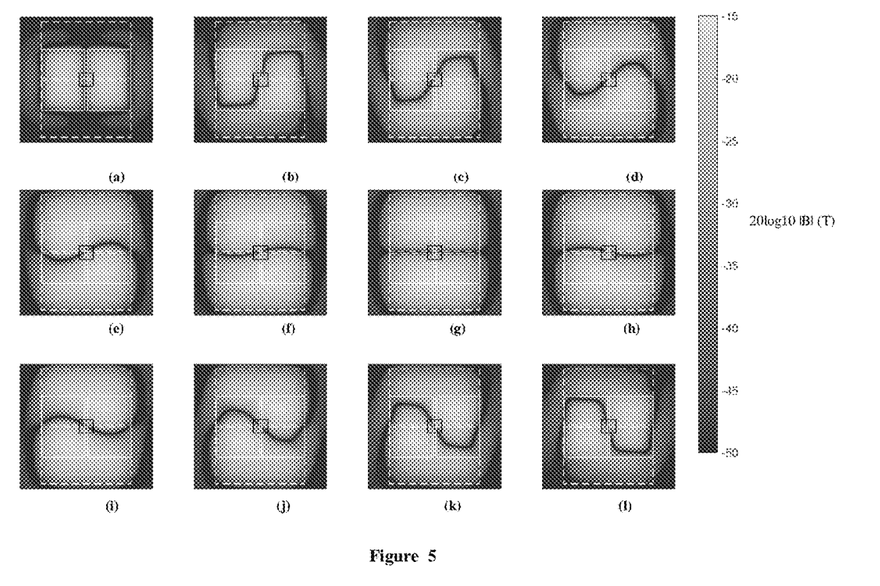
FIG. 5, shows the magnitude of the magnetic field for various rotation angles of the FFL generated by the coil system shown in FIG. 4 for (a) 0°, (b) 15°, (c) 30°, (d) 45°, (e) 60°, (f) 75°, (g) 90°, (h) 105° (i) 120° (j) 135° (k) 150° (l) 165° FFL angles.

In FIG. 5, FFL rotation is simulated for a rectangular coil system similar to the one given in FIG. 4 in 15 degree steps.

The figures are given on the plane generated by the x (3) and y (4) axes (xy-plane). The solid white line shows the position of coil group (1), and the dashed white line show the position of coil group (2). The black solid line shows the volume in which the FFL is a straight line and the rate of change of magnetic field as a function of position (FFL gradient) is constant for all rotation angles. This is the primary field of view, in which the performance of the MPI (i.e, image resolution, sensitivity) is maximum. Nevertheless, FFL extends to a larger volume and imaging is still practical. The extent of the field of view depends on the allowable degradation on FFL gradient for the performance requirements of the imaging system.

To generate 2D images on the xy-plane, FFL should also be scanned/translated in the direction perpendicular to the FFL (14) for each rotation angle (15) using a time-varying drive field. This drive field will be called as xy-drive field in the remainder of the present discussion. Z-axis (5) and x-axis (3) views for an embodiment enabling electronic translation and rotation are given in FIG. 6a and FIG. 6b, respectively. X-axis cut is shown on the plane depicted by (11). To translate the FFL perpendicular to the FFL axis (12), a homogeneous field is generated using a Helmholtz coil pair (13a, 13b) on the z-axis (5). This coil pair can also be used to enlarge the field of view (16) (imaging space), i.e. as focus field generator. Since the drive magnetic field is parallel to the z-axis (5), the magnetization of the SPIO nanoparticles is also in the z-direction. Therefore, receive coil(s) should be sensitive in the z-direction to obtain the response of the nanoparticles. (13) can also be used as the receiver coil. Alternatively, separate drive field, focus field and receive coils can be used in this axis without violating the open bore requirement.

Figure 6A:
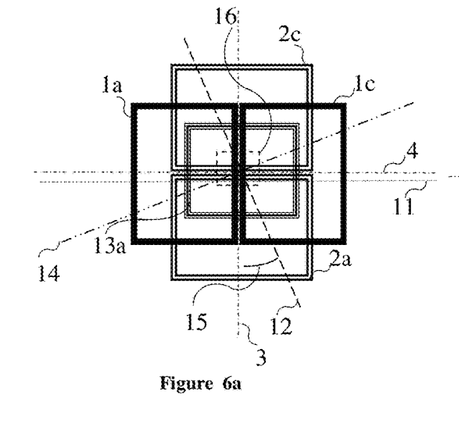
FIG. 6a shows an embodiment of the drive field coils integrated to the selection field coil system to scan/translate the FFL in the plane parallel to the plane generated by x- and y-axes, looking from z-axis.
Figure 6B:
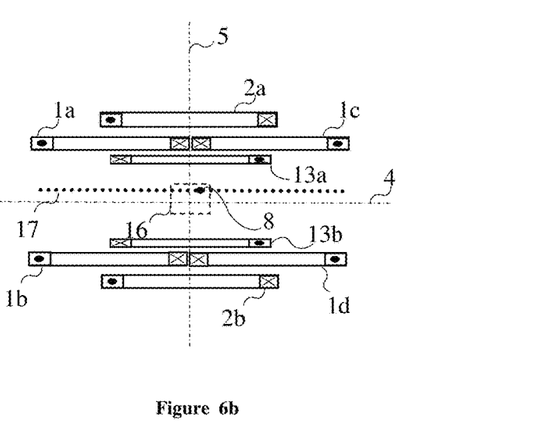
FIG. 6b shows an embodiment of the drive field coils integrated to the selection field coil system to scan/translate the FFL in the plane parallel to the plane generated by x- and y-axes, looking from x-axis.

The position of the imaging plane in the z-axis (17) can be selected by changing the excitation amplitude ratio of the upper (1a, 2a, 1c, 2c) and lower (1b, 2b, 1d, 2d) selection field coils. If this ratio is one, the FFL and the imaging plane, is on the mid-plane between the upper (1a, 2a, 1c, 2c) and lower (1b, 2b, 1d, 2d) coils. If the excitation amplitude of the upper coils (1a,2a,1c,2c) is higher than the one of the lower coils (1b,2b,1d,2d), the imaging plane is closer to the lower coils (1b,2b,1d,2d) on the z-axis (5). If the excitation amplitude of the upper coils (1a,2a,1c,2c) is lower than the one of the lower coils (1b,2b,1d,2d), the imaging plane (17) is closer to the upper coils (1a,2a,1c,2c) on the z-axis (5). This situation is shown in FIG. 6b. Required excitation amplitudes for the upper (1a, 2a, 1c, 2c) and lower coils (1b, 2b, 1d, 2d) for a desired imaging plane position can be determined using analytical and/or numerical magnetic field calculation methods. FIG. 6 shows the preferred embodiment for which z-axis (5) slice selection is possible with the proposed configuration. Selection Field coils (1,2) are used to generate the FFL, rotate the FFL around the z-axis (5), translate the FFL in the z-axis direction. The drive field coils (13) are used to drive the FFL on any plane parallel to the plane generated by x (3) and y (4) axes to excite the SPIO nanoparticles in the field of view. These coils are also used to shift the center of the field of view to extend the imaging volume.

Figure 7A:
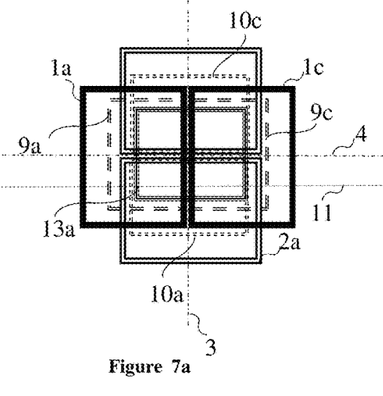
FIG. 7a shows an embodiment of the drive field coils integrated to the selection field coil system to scan/translate the FFL in any direction perpendicular to the FFL axis (12), looking from z-axis.
Figure 7B:
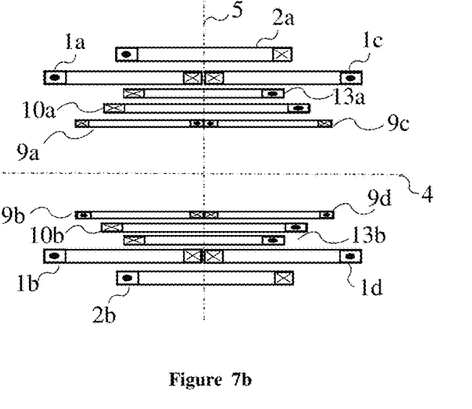
FIG. 7b shows an embodiment of the drive field coils integrated to the selection field coil system to scan/translate the FFL in any direction perpendicular to the FFL axis (12), looking from z-axis.
Figure 8:
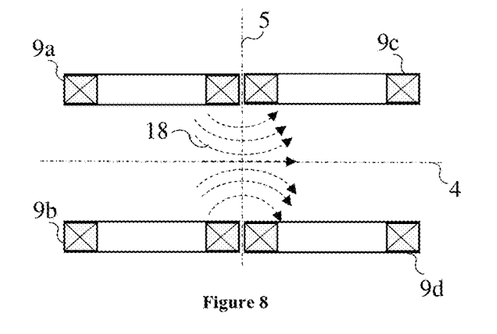
FIG. 8 shows an embodiment of the drive field coil to generate a magnetic field in the y-axis direction and respective magnetic field lines.
Figure 9:
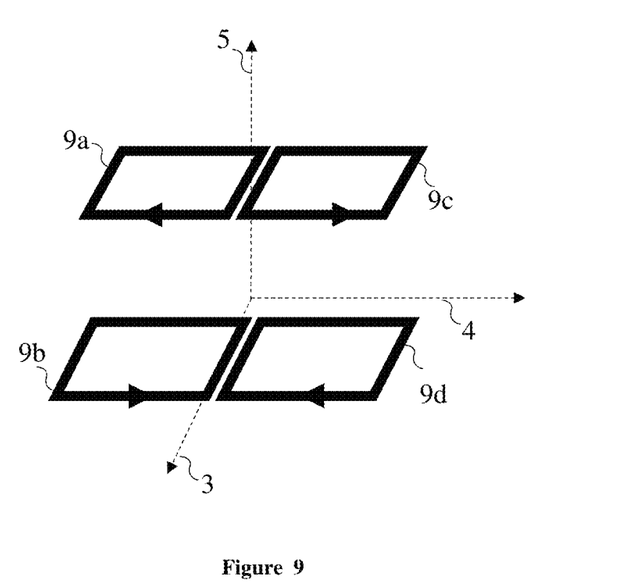
FIG. 9 shows an embodiment of the drive field coil group to generate a magnetic field in the y-axis direction and respective magnetic field lines.

Imaging in three dimensions is possible by scanning the imaging plane on the z-axis (5) and performing two dimensional imaging on each imaging plane with electronic rotation and translation as described above. Since there is no drive field in the z-axis (5) direction, image resolution in the in the z-axis (5) direction is lower than the image resolution on the plane generated by the x (3) and y (4) axes. The resolution of the images on the z-axis (5) direction can be improved by scanning the FFL on the z-axis using a time-varying drive field, which will also translate the FFL in the z-axis direction. This drive field will be called the z-drive field in the remainder of this document. This can be done by applying alternating current to the upper (1*a*, 2*a*, 1*c*, 2*c*) and lower (1*b*, 2*b*, 1*d*, 2*d*) selection field coils. The amplitude of this alternating current is much smaller than the current required for generating the static (selection field) magnetic field. An alternative embodiment is using an external z-drive field coil system similar to the selection field coil system. This embodiment is shown in FIGS. 7*a* and 7*b* looking from the z-axis (5) and x-axis (3) at plane (11), respectively. Coil groups (9) and (10) generate the drive field necessary for the FFL scan in the z-axis (5) direction. The current directions of the coil groups (9) and (10) are arranged so that the magnetic fields induced by the upper (9*a*, 9*c*, 10*a*, 10*c*) and lower (9*b*, 9*d*, 10 *b*, 10*d*) coils add constructively in the field of view. Coil group (9) generates a time varying magnetic field in the y-axis (4) direction. This is illustrated in FIG. 8. The coil current directions that generate the magnetic field (18) are shown in FIG. 9. Similarly, coil group (10) generates a time varying magnetic field in the x-axis (3) direction. The excitations amplitudes of the coil groups (9) and (10) should be arranged so that the drive magnetic field direction is parallel to the FFL direction (12), i.e. z-drive field direction should be rotated to the angle (15) in a similar way described for the FFL rotation direction. This embodiment may be preferred as it releases the low frequency restriction present in the case where SF coils are used to generate the z-drive field. The z-drive field can also be generated using only upper (9*a*, 9*c*, 10*a*, 10*c*) or lower (9*b*, 9*d*, 10 *b*, 10*d*) coils. The field amplitude decreases towards the opposite side (in which the drive coils are not present) in this case, increasing the requirement for the coil current amplitude.

Figure 10:
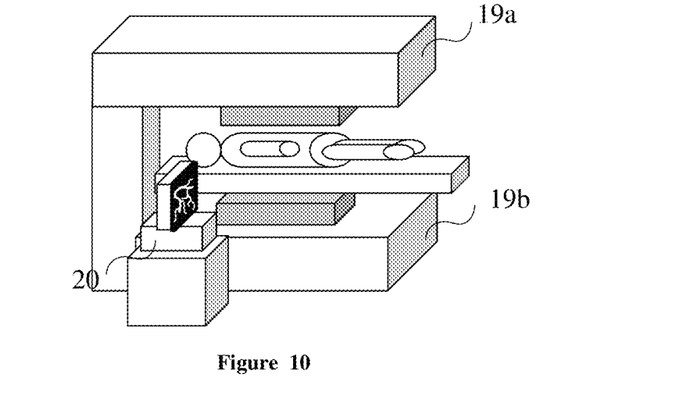
FIG. 10 shows an embodiment of the clinical MPI system in which the proposed coil system is used.

Using the methods described above, the FFL (8) can be translated and scanned on any plane parallel to the plane generated by the x (3) and y (4) axes, and also on the z-axis direction (5) electronically. The FFL can also be rotated inside the FOV (16) fully electronically without the need for a mechanical rotation. The coils can be optimized according to required resolution and FOV size by a person skilled in the art. Since all the coils are parallel, there is no obstruction on the sides making the patient/object accessible during MPI FFL data acquisition/imaging process. The field of view of the imaging system on and parallel to the plane generated by x (3) and y (4) axes depend on the coil design and can accommodate large subjects such as human body. An illustration of the clinical usage is shown in FIG. 10. The patient lies between upper (19*a*) and lower (19*b*) parts of the imaging system. (19*a*) and (19*b*) include all the necessary coils and hardware to scan the field of view, which can be selected using the computer control (20).

Figure 11:
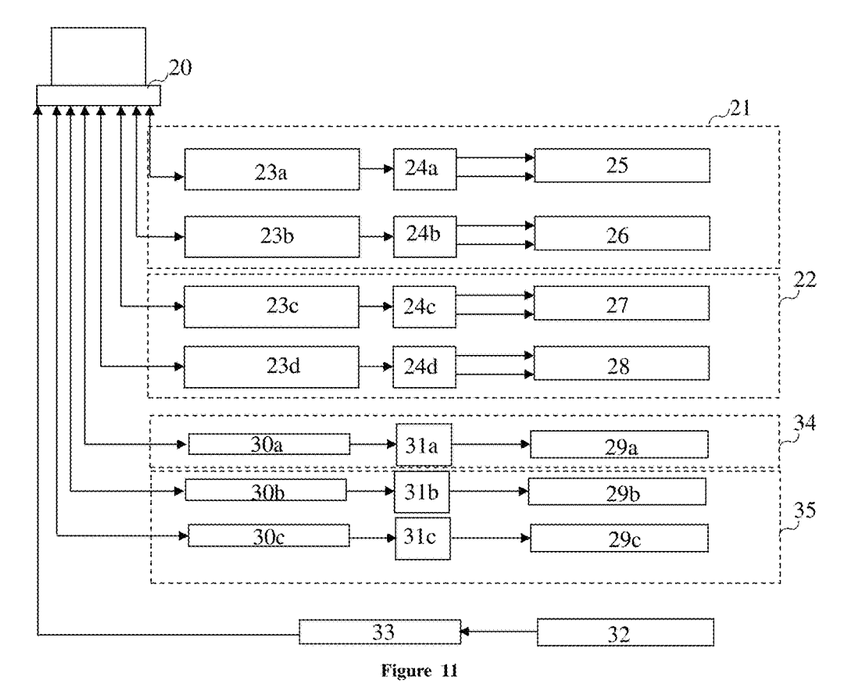
FIG. 11 shows an example transmit and receive system for the proposed coil setup.

The preferred embodiment for the described MPI system is shown in FIG. 11. Computer control (20) includes a user interface to select imaging volume and parameters. Image sequence planning is also performed by (20). The selection field is generated using the selection field transmit units (21) and (22). The selection field transmit units are used to generate and rotate the FFL at the desired z-axis position on the plane perpendicular to the z-axis (5). Each selection field transmit unit includes a power supply (23*a*, 23*b*, 23*c*, 23*d*), transmit circuitry (24*a*, 24*b*, 24*c*, 24*d*) including necessary components such as filters and transmission wires, and selection field coils pairs (25, 26, 27, 28). The computer (20) controls and monitors the currents sent to the selection field coils (1, 2). As described above and given in FIG. 1, the magnitude of the currents in the upper (or lower) selection field coils is equal, while their signs are opposite (I1*a*=−I1*c*, I1*b*=−I1*d*, I2*a*=−I2*c*, I2*b*=−I2*d*). Therefore, at least two power supplies (23) are required per coil group. In the preferred embodiment, upper coil pairs of coil group 1 (1*a*, 1*c*), which are represented by (25) in FIG. 10, are fed by the power supply (23*a*) via transmit circuitry (24*a*). Lower coil pairs of coil group 1 (1*b*, 1*d*), which are represented by (26) in FIG. 10, are fed by the power supply (23*b*) via transmit circuitry (24*b*). Upper coil pairs of coil group 2 (2*a*, 2*c*), which are represented by (27) in FIG. 10, are fed by the power supply (23*c*) via transmit circuitry (24*c*). Lower coil pairs of coil group 1 (1*b*, 1*d*), which are represented by (28) in FIG. 10, are fed by the power supply (23*d*) via circuitry (24*d*). Alternatively, each selection field coil can be fed by a separate power supply. The output currents from the power supplies are monitored to make sure the system is working properly. This is also required to detect possible failures.

The xy- and z-drive fields are generated using the drive field transmit units (34) and (35). The timing and magnitudes of the drive field excitations are planned before the imaging procedure using the control computer (20). Drive field transmit unit (34) is used to translate/scan the FFL on the plane that FFL is located parallel to the plane generated by the x (3) and y (4) axes (xy-drive field) to excite the SPIO nanoparticles in the field of view. (34) can also be used as the focus field generator to shift the center of the field of view on the plane that FFL is located parallel to the plane generated by the x (3) and y (4) axes. The drive field transmit unit (34) includes a waveform generator (30*a*), drive field transmit circuitry (31*a*), and drive field coil(s) (29*a*). Drive field transmit circuitry (31*a*) includes components such as amplifier(s), matching circuit(s), filter(s) to supply the required current to generate the drive field. The waveform generator (30*a*) output (amplitude, frequency, waveform, etc.) is controlled by the controlling unit (20) for the required FFL direction and field of view. Drive field can be generated by a Helmholtz coil arrangement as given in FIGS. 6 and 7 using coils (13*a*) and (13*b*). In this case (29*a*) comprises of (13*a*) and (13*b*). Drive field transmit unit (35) is used to translate/scan the FFL in the z-axis (5) direction to excite the SPIO nanoparticles in the field of view (z-drive field). Waveform generators (30*b*) and (30*c*) are used to supply time varying voltage/current to excite the drive field coils (29*b*) and (29*c*), respectively. The waveform generator (30*b*, 30*c*) outputs (amplitude, frequency, waveform, etc.) are controlled by the controlling unit (20) for the required FFL direction and field of view. Transmit circuitries (31*b*) and (31*c*) includes components such as amplifier(s), matching circuit(s), filter(s) to supply the required current to the drive coils (29*b*) and (29*c*).

On the receiver side, receiver coil(s) (32) are used to detect the SPIO nanoparticle response to the applied drive field(s). The receiver coil(s) are positioned around the FOV and oriented such that they pick up the time-varying magnetic field of SPIO nanoparticles. Although auxiliary receiver coil(s) can be used in the system, the drive field coil(s) (29*a*, 29*b*, 29*c*) can also be used as receive coil(s). The signal induced in the receiver coil(s) (32) is amplified and filtered firstly, and then digitized using an analog to digital converter (ADC) using a receiver circuit (33). The received data is then processed to generate the MPI image (s).

To reconstruct the images from the received data, a radon transform based algorithm similar to the one used in the CT imaging (T. Knopp, M. Erbe, T. F. Sattel, S. Biederer, and T. M. Buzug, "A Fourier slice theorem for magnetic particle imaging using a field-free line," Inverse Problems, vol. 27, no. 9, p. 095004, 2011.) can be used. Alternatively, system matrix method (J. Rahmer, J. Weizenecker, B. Gleich, and J. Borgert, "Signal encoding in magnetic particle imaging: Properties of the system function," BMC Med. Imag., vol. 9, p. 4, April 2009) can also be employed. In the Radon transform based method, it is assumed that the gradient and linearity of the FFL is not affected from rotation and translation of the FFL, putting a restriction in the coil design. In the system matrix method, a small test object with a known nanoparticle concentration is scanned throughout the FOV volume and the received data is recorded at each position of the object. By this way, a calibration system matrix is generated. The SPIO concentration of the patient/object is obtained using this data. Alternatively, the magnetic field of the system can be measured and/or simulated for various rotation angles and translation distances of the FFL, and radon transform can be performed using this data relaxing the need for uniform FFL gradient and linearity throughout the FOV. This method may be more efficient and accurate, since a large system matrix is not required and there is no assumption on the linearity and gradient of the FFL.

The selection field coils groups can be implemented with interleaved windings, rather than using separated coil groups separated at different vertical positions.

Figure 12:
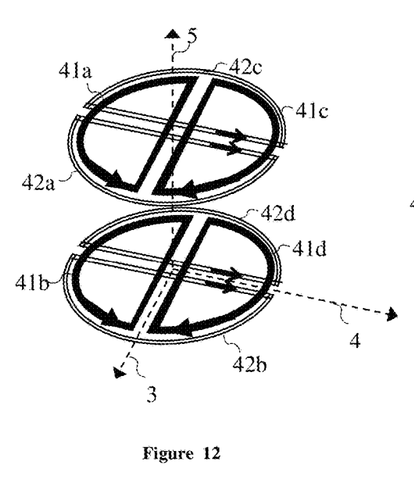
FIG. 12 shows a D-type coil system similar to the one shown in FIG. 1, and respective current directions enabling to generate, rotate and translate a field free line for MPI.
Figure 13:
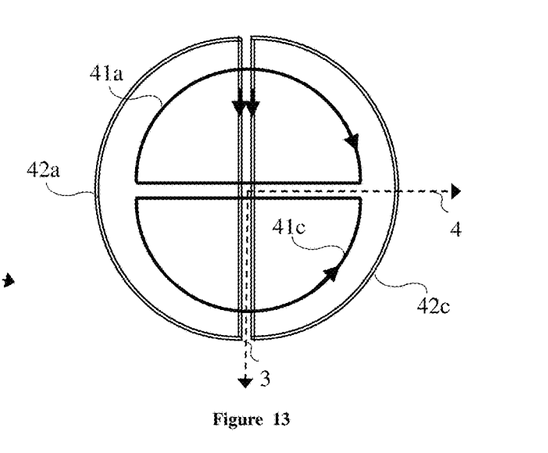
FIG. 13 shows the z-axis view of the coil system shown in FIG. 12.

Any geometry for the coils can be chosen even though a rectangular geometry is used in this document. In fact, the geometry should be optimized to obtain the best FFL performance with minimum power consumption. A coil system in which D type coils (41,42) are used is shown in FIGS. 12 and 13.

Figure 14:
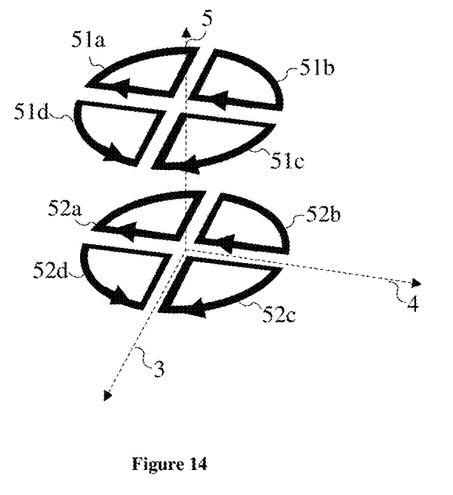
FIG. 14 shows a single layer coil system consisting of 90 degrees sectoral coils, enabling to generate, rotate and translate a field free line for MPI.
Figure 15:
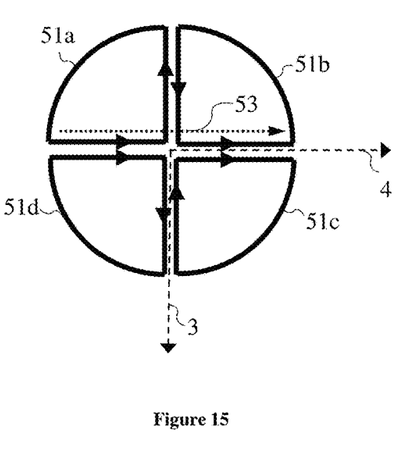
FIG. 15 shows the z-axis view of the coil system shown in FIG. 14.

Rather than using multilayered coil groups, FFL can also be generated, rotated and moved using single layer coil arrays. An embodiment, in which four coil pairs are used, is shown in FIG. 14. By adjusting the currents of each coil (51a-d, 52a-d), FFL can be generated in any direction. If the coils are excited with equal amplitude and with directions shown in FIG. 15, an FFL can be generated in the y-axis (4) direction. Note that the currents in the x-axis (3) direction cancel each other, while currents in the y-axis (4) direction combine constructively. The advantage of this embodiment is less power consumption compared to the embodiments shown in FIG. 1, since all the coils are on the same z-plane (5). In the multilayered configuration, upper layers require more current to generate the same magnetic field gradient, as they are farther away from the field of view. However, there is a restriction on the thickness of the coils (51, 52) for field uniformity. For example the cancellation of the magnetic fields created by the currents on the x-axis (3) of FIGS. 14 and 15, depend on the proximity of the wires carrying these currents.

Figure 16:
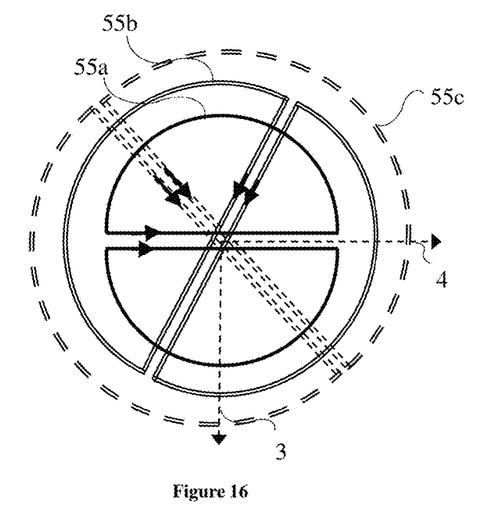
FIG. 16 shows the z-axis view of a three-layer coil system consisting of 60 degree rotated D type coils, enabling to generate, rotate and translate a field free line for MPI.

In the given embodiment, the coil system includes two coil groups rotated 90 degrees with respect to each other in the horizontal plane. In general, more coil groups (e.g. three coil groups rotated 60 degrees with respect to each other) can be used to increase the gradient and linearity of the FFL as a function of rotation. An example embodiment using three coil groups (55a, 55b, 55c) rotated 60 degrees with respect to each other in the horizontal plane is shown in FIG. 16.

It is possible to implement a multiple FFL coil system for MPI using the building selection field and/or drive field blocks of the present invention, which is an FLL generating coil system (FIG. 2).

While a specific embodiment of the invention has been shown and described in detail to illustrate the application of the principles of the invention, it will be understood that the invention may be embodied otherwise without departing from such principles.

What is claimed is:

1. An open bore coil system for enabling electronic steering and rotation of a Field Free Line (FFL) inside a volume, comprising:
   a first coil group (1), the first coil group (1) comprising a first coil (1a), a second coil (1b), a third coil (1c), and a fourth coil (1d), the first coil (1a), the second coil (1b), the third coil (1c), and the fourth coil (1d) being fed with respective first current (I1a), second current (I1b), third current (I1c), and fourth current (I1d); and
   a second coil group (2), the second coil group (2) comprising a first coil (2a), a second coil (2b), a third coil (2c), and a fourth coil (2d), the first coil (2a), the second coil (2b), the third coil (2c), and the fourth coil (2d) being fed with respective first current (I2a), second current (I2b), third current (I2c), and fourth current (I2d),
   wherein the coils in the respective first coil group (1) and second coil group (2) are located as coil pairs placed side by side and fed with alternating current directions,
   wherein the first coil (1a) and the second coil (1b) of the first coil group (1) form a first coil pair (1a-1b), the first coil pair (1a-1b) being fed with the same current direction, thereby generating a magnetic field in a first z-direction (6), the first z-direction (6) being selected from the group consisting of +z and −z,
   wherein the third coil (1c) and the fourth coil (1d) of the first coil group (1) form a second coil pair (1c-1d), the second coil pair (1c-1d) being fed with an opposite current direction with respect to the first coil (1a) and the second coil (1b) of the first coil group (1), thereby generating a magnetic field in a second z-direction (7) selected from the group consisting of +z and −z, the second z-direction (7) being the opposite direction of the first z-direction (6), wherein if the first z-direction (6) is +z, then the second z-direction (7) is −z, and if the first z-direction (6) is −z, then the second z direction (7) is +z,
   wherein the x component (3) and the y component (4) of the magnetic field vanish on a planar or non-planar surface between a top coil pair (1a-1c), the top coil pair (1a-1c) comprising first coil (1a) and third coil (1c) and a bottom coil pair, the bottom coil pair (1b-1d) comprising second coil (1b) and fourth coil (1d),
   wherein the z-axis component of the magnetic field vanishes on a planar or non-planar surface between the first coil pairs (1a-1b) and the second coil pair (1c-1d), and
   wherein the second coil group (2) is rotated around the z-axis with respect to the first coil group (1) at a rotation angle of theta degrees.

2. The open bore coil system according to claim 1, wherein the rotation angle theta is 90 degrees.

3. The open bore coil system according to claim 1, wherein the windings of the first and second coil groups are interleaved.

4. The open bore coil system according to claim 1, wherein the path of the coil windings is rectangular.

5. The open bore coil system according to claim 1, wherein the path of the coil windings is semi-circular.

6. The open bore coil system according to claim 1, further comprising additional one or more coil groups each rotated around the z-axis with a rotation angle 180 degrees divided by the number of coil groups, with respect to each other.

7. The open bore coil system according to claim 1, wherein the design of the coils of the second coil group (2) is different from the design of the coils of the first coil group (1).

8. The open bore coil system according to claim 1, wherein if the second coil group (2) is not excited, the FFL is generated on the x axis (3) and θ=0 degrees.

9. The open bore coil system according to claim 1, wherein if the first coil group 1 (1) is not excited, the FFL is generated on the y axis (4) and θ=90 degrees.

10. The open bore coil system according to claim 1, wherein to rotate the FFL θ degrees (15) with respect to x-axis (3), the excitation for the coils in the first coil group (1) is $I1a=I1b=-I1c=-I1d=I_1 \cos(phi)$ and the excitation of the coils in the second coil group (2) is $I2a=I2b=-I2c=-I2d=I_2 \sin(phi)$.

11. The open bore coil system according to claim 1, wherein the first coil group (1) and the second coil group (2) are placed on different positions on the z-axis (5).

12. The open bore coil system according to claim 1, wherein all the coils are parallel.

13. A magnetic particle imaging system, comprising:
a computer control (20);
a first selection field transmit unit (21) and a second selection field transmit unit (22), the first selection field transmit unit (21) and a second selection field transmit unit (22) adapted to generate and rotate a Field Free Line (FFL) at a desired z-axis position on a plane perpendicular to a z-axis (5),
wherein each of the first selection field transmit unit (21) and a second selection field transmit unit (22) includes a plurality of power supplies each associated with transmit circuitry, the plurality of power supplies and associated transmit circuitries comprising at least a first power supply (23a) associated with a first transmit circuitry (24a), a second power supply (23b) associated with a second transmit circuitry (24b), a third power supply (23c) associated with a third transmit circuitry (24c), and a fourth power supply (23d) associated with a fourth transmit circuitry (24d),
a first selection field coil group (1), the first selection field coil group (1) comprising a first selection field coil (1a), a second selection field coil (1b), a third selection field coil (1c), and a fourth selection field coil (1d), the first selection field coil (1a), the second selection field coil (1b), the third selection field coil (1c), and the fourth selection field coil (1d) being fed with respective first current (I1a), second current (I1b), third current (I1c), and fourth current (I1d); and
a second selection field coil group (2), the second selection field coil group (2) comprising a first selection field coil (2a), a second selection field coil (2b), a third selection field coil (2c), and a fourth selection field coil (2d), the first selection field coil (2a), the second selection field coil (2b), the third selection field coil (2c), and the fourth selection field coil (2d) being fed with respective first current (I2a), second current (I2b), third current (I2c), and fourth current (I2d),
wherein the computer control (20) is adapted to control and monitor currents applied to the selection field coils (1a, 1b, 1c, 1d, 2a, 2b, 2c, 2d),
wherein the first selection field coil (1a) of the first selection field coil group (1) and the third selection field coil (1c) of the first coil group (1) are upper selection field coils, and the second selection field coil (1b) of the first coil group (1) and the fourth selection field coil (1d) of the first coil group (1) are lower selection field coils,
wherein the second selection field coil (2a) of the second selection field coil group (2) and the third selection field coil (2c) of the second coil group (2) are upper selection field coils, and the second selection field coil (2b) of the second coil group (2) and the fourth selection field coil (2d) of the second coil group (2) are lower selection field coils, and
wherein the magnitudes of the currents in the upper selection field coils (1a, 1c) of the first selection field coil group (1) are equal, while their signs are opposite, and the magnitudes of the currents in the lower selection field coils (1b, 1d) of the first selection coil group (1) are equal, while their signs are opposite ($I1a=-I1c$, $I1b=-I1d$, $I2a=-I2c$, $I2b=-I2d$).

14. The system according to claim 13, wherein the upper selection field coils (1a, 1c), are fed by the first power supply (23a) via the first transmit circuitry (24a) and the lower selection field coils (1b, 1d) are fed by the second power supply (23b) via the second transmit circuitry (24b), and wherein the upper selection field coils (2a, 2c) of the second selection field coil group (2) are fed by the third power supply (23c) via the third transmit circuitry (24c), and the lower selection field coils (2b, 2d) of the second selection field coil group (2) are fed by the fourth power supply (23d) via the third transmit circuitry (24d).

15. The system according to claim 13, wherein each selection field coil (1a, 1b, 1c, 1d, 2a, 2b, 2c, 2d) is fed by a separate power supply.

16. The system according to claim 13, wherein the power supplies (23) and transmit circuitry (24) are adapted to generate a time-varying signal to translate/scan the FFL in a z-axis (5) direction.

17. The system according to claim 13, further comprising a drive field transmit unit (34) adapted to translate/scan the FFL on a plane parallel to the plane generated by an x axis (3) and a y axis (4).

18. The system according to claim 17, wherein the drive field transmit unit (34) is a focus field generator adapted to shift a center of a field of view on the plane parallel to the plane generated by an x axis (3) and a y axis (4).

19. The system according to claim 18, wherein the drive field transmit unit (34) further comprises a waveform generator (30a), drive field transmit circuitry (31a), and at least one drive field and/or focus field coil (29a).

20. The system according to claim 19, wherein at least one drive field and/or focus field coil (29a) comprises a Helmholtz coil arrangement (13a, 13b).

21. The system according to claim 19, further comprising a second drive field transmit unit (35) adapted to translate/scan the FFL in a z-axis (5) direction to excite the SPIO nanoparticles in a z-drive field.

22. The system according to claim 21, wherein the second drive field transmit unit (35) further comprises a first waveform generator (30b), a second waveform generator (30c), a first drive field transmit circuitry (31b) associated with the first waveform generator (30b), a second drive field transmit circuitry (31c) associated with the second waveform generator (30c), a first drive field coil (29b) associated with the first drive field transmit circuitry (31b), and a second drive field coil (29c) associated with the second drive field transmit circuitry (31c).

23. The system according to claim 13, comprising at least one receiver coil (32) to receive the magnetization signals generated by the SPIOs.

24. The system according to claim 23, further comprising a receiver circuitry (33) to amplify, filter and digitize the received signal via receiver coil(s) (32).

25. An open bore coil system for magnetic particle imaging, enabling electronic steering and rotation of a Field Free Line (FFL) and exciting magnetic particles inside a volume, comprising:
- a first coil group with two layers of sectoral coil arrays two layers of coils, wherein each layer comprising a plural number of sectoral coils, wherein each sectoral coil has at least two edges adjacent to one edge of each of the two adjacent coils, and the current directions and amplitudes of the coils are arranged such that the magnetic field vanishes inside a desired tubular volume on a planar or-non planar surface between the layers of the sectoral coil arrays;
- a second coil group, generating homogeneous oscillating magnetic field in one or more directions inside a volume to excite magnetizable particles and translate the field free line inside the imaging volume; and
- a third coil group generating homogeneous magnetic field inside a volume to steer the field free line to extend the field of view of the imaging volume.

* * * * *